United States Patent
Draper et al.

(10) Patent No.: US 9,990,122 B2
(45) Date of Patent: Jun. 5, 2018

(54) ELECTRONICALLY CONTROLLED DRUG DELIVERY DEVICE WITH TOUCH SCREEN

(71) Applicant: SANOFI-AVENTIS DEUTSCHLAND GMBH, Frankfurt am Main (DE)

(72) Inventors: Paul Richard Draper, Worcestershire (GB); Joseph Butler, Warwickshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 359 days.

(21) Appl. No.: 14/763,867

(22) PCT Filed: Jan. 27, 2014

(86) PCT No.: PCT/EP2014/051471
§ 371 (c)(1),
(2) Date: Jul. 28, 2015

(87) PCT Pub. No.: WO2014/118108
PCT Pub. Date: Aug. 7, 2014

(65) Prior Publication Data
US 2015/0363097 A1  Dec. 17, 2015

(30) Foreign Application Priority Data

Jan. 29, 2013 (EP) ..................... 13153138

(51) Int. Cl.
*G06F 3/0484* (2013.01)
*A61M 5/142* (2006.01)
(Continued)

(52) U.S. Cl.
CPC ......... *G06F 3/04847* (2013.01); *A61M 5/142* (2013.01); *A61M 5/172* (2013.01);
(Continued)

(58) Field of Classification Search
CPC .... G06F 3/04847; G06F 3/0416; G06F 3/044; G06F 3/045; G06F 3/0421; G06F 3/043;
(Continued)

(56) References Cited

U.S. PATENT DOCUMENTS

2002/0166944 A1* 11/2002 Foreman ................. E04G 11/02
249/11
2004/0158193 A1  8/2004 Bui et al.
(Continued)

FOREIGN PATENT DOCUMENTS

WO  2011/023628  3/2011
WO  2012/072559  6/2012

OTHER PUBLICATIONS

European Search Report for EP App. No. 13153138.6, dated Aug. 29, 2013.
(Continued)

*Primary Examiner* — Anil Bhargava
(74) *Attorney, Agent, or Firm* — Fish & Richardson P.C.

(57) ABSTRACT

The invention relates to an electronically controlled drug delivery device for administering a dose of a drug, comprising a body with a touchscreen and a control unit for controlling the touchscreen and operation of the drug delivery device related to delivery of the dose.

7 Claims, 3 Drawing Sheets

(51) Int. Cl.
*A61M 5/20* (2006.01)
*G06F 3/043* (2006.01)
*G06F 3/044* (2006.01)
*G06F 3/045* (2006.01)
*G06F 3/0488* (2013.01)
*A61M 5/172* (2006.01)
*G06F 3/041* (2006.01)
*G06F 3/042* (2006.01)
*A61K 38/00* (2006.01)

(52) U.S. Cl.
CPC ............... *A61M 5/20* (2013.01); *G06F 3/043* (2013.01); *G06F 3/044* (2013.01); *G06F 3/045* (2013.01); *G06F 3/0416* (2013.01); *G06F 3/0421* (2013.01); *G06F 3/04886* (2013.01); *A61K 38/00* (2013.01); *A61M 2005/2073* (2013.01); *A61M 2205/50* (2013.01); *A61M 2205/505* (2013.01)

(58) Field of Classification Search
CPC ............... G06F 3/04886; A61M 5/172; A61M 2205/505
See application file for complete search history.

(56) References Cited

U.S. PATENT DOCUMENTS

| | | |
|---|---|---|
| 2004/0225252 A1 | 11/2004 | Gillespie et al. |
| 2006/0184121 A1 | 8/2006 | Brockman et al. |
| 2008/0114299 A1* | 5/2008 | Damgaard-Sorensen ................ G06F 19/3406 604/131 |
| 2009/0030366 A1 | 1/2009 | Hochman |
| 2010/0100037 A1* | 4/2010 | Cozmi ................. A61M 5/142 604/67 |
| 2010/0185183 A1* | 7/2010 | Alme ................. A61M 5/14276 604/891.1 |
| 2012/0030610 A1 | 2/2012 | Diperna et al. |
| 2013/0079708 A1* | 3/2013 | Wimpenny ........... A61M 5/002 604/65 |
| 2014/0184511 A1* | 7/2014 | Puustinen ........... G06F 3/04886 345/168 |

OTHER PUBLICATIONS

International Search Report and Written Opinion for Int. App. No. PCT/EP2014/051471, dated May 12, 2014.

\* cited by examiner

ELECTRONICALLY CONTROLLED DRUG DELIVERY DEVICE WITH TOUCH SCREEN

CROSS REFERENCE TO RELATED APPLICATIONS

The present application is a U.S. National Phase Application pursuant to 35 U.S.C. § 371 of International Application No. PCT/EP2014/051471 filed Jan. 27, 2014, which claims priority to European Patent Application No. 13153138.6 filed Jan. 29, 2013. The entire disclosure contents of these applications are herewith incorporated by reference into the present application.

TECHNICAL FIELD

The invention relates to an electronically controlled drug delivery device for administering a dose of a drug.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring. In other devices this is achieved by an electromechanical drive. Devices with electromechanical and/or electronic components may comprise a drive for electrically displacing a bung within the cartridge or syringe.

SUMMARY

It is an object of the present invention to provide an improved electronically controlled drug delivery device for administering a dose of a drug.

The object is achieved by an electronically controlled drug delivery device for administering a dose of a drug according to claim 1.

Preferred embodiments of the invention are given in the dependent claims.

According to the invention an electronically controlled drug delivery device for administering a dose of a drug comprises a body with a touchscreen and a control unit for controlling the touchscreen and operation of the drug delivery device related to delivery of the dose.

A touchscreen is a powerful means for user interaction. Touchscreens enable a user interface with a customisable set of icons, buttons and interaction points. This allows the interaction points to be in alternative screen zones in different device modes; it also allows devices to have user interfaces tailored to specific user groups, e.g. geriatric and pediatric software versions. In addition, 'gestures' are possible with touchscreen systems, for controlling, scrolling, zooming, etc.; which are useful for devices with history and graph type functionality.

In an exemplary embodiment the control unit is configured to split the touchscreen into at least two distinct zones which, when operated, cause distinct actions. This may reduce the risk for inadvertent user operation which may arise if all controls such as buttons and control elements are located in close proximity on the touch screen.

In an exemplary embodiment the control unit is configured to split the touchscreen into at least three distinct zones thus further enhancing the options for operating the drug delivery device.

In an exemplary embodiment the control unit is configured to provide a control element for dose setting, e.g. a dial, radio buttons, slide control, scroll bar, toggle button, drop down list etc., in one of the zones and to provide a button for triggering delivery of the set dose of the drug in another one of the zones.

In an exemplary embodiment the control unit is configured to provide a control element for dose setting, e.g. a dial, radio buttons, slide control, scroll bar, toggle button, drop down list etc., in one of the zones and to provide a button for confirming the set dose in another one of the zones and to provide a button for triggering delivery of the set dose of the drug in yet another one of the zones.

In an exemplary embodiment the control unit is configured to switch the control element or button in at least one of the zones between an active state and an inactive state In an exemplary embodiment the control unit is configured to switch the control element or button in at least one of the zones between an active state and an inactive state depending on previous operation of at least one of the other zones thus reducing the risk of inadvertent operation by encouraging the user to adhere to a particular sequence of operation.

In an exemplary embodiment the control unit is configured to render the control element or button visible in the active state and invisible in the inactive state.

In another exemplary embodiment the control unit is configured to render the control element or button dimmed or shaded in the inactive state relative to its appearance in the active state. Likewise the active and inactive state may be distinguished by different colours.

In an exemplary embodiment the control unit is configured to render the button for triggering delivery of the set dose active only after operation of the button for confirming the set dose thus encouraging the user to set a dose or become aware of the currently set dose before triggering delivery.

In an exemplary embodiment the control unit comprises a timer for setting a time period, wherein the control unit is configured to start the timer after operation of one of the zones and to switch the control element or button of at least one of the other zones from the inactive state to the active state after expiration of the set time period. Thus a minimum time period is required between user steps, thereby eliminating the chance of the user accidentally "swiping" across more than one zone and inadvertently actuating them.

The touchscreen may be arranged as a surface acoustic wave touchscreen, capacitive touchscreen, a resistive touchscreen, an optical touchscreen, e.g. based on an infrared grid, infrared acrylic projection or optical imaging. Further options comprise disperse signal technology and acoustic pulse recognition.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
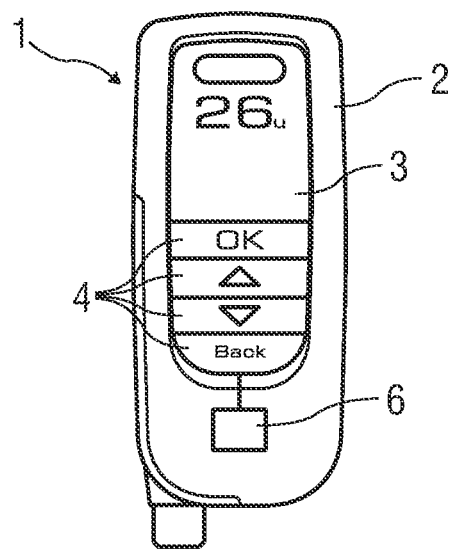
FIG. 1 is a schematic view of an exemplary embodiment of an electronically controlled drug delivery device with a touch screen.

FIG. 1 is a schematic view of an exemplary embodiment of an electronically controlled drug delivery device 1. The drug delivery device 1 comprises a body 2 having a touchscreen 3 for providing an interface to a user.

The body 2 is adapted to receive a drug cartridge (not illustrated). A hypodermic needle may be attached to the cartridge, preferably a needle with two tips, one of them for piercing an injection site and the other for piercing the septum on the cartridge for establishing a fluid communication between the cartridge and the needle. The drug delivery device 1 may further comprise at least one electric unit or electronic device (not illustrated) such as a control unit and/or an electromechanical drive (not illustrated) for inserting the needle into an injection site, e.g. a patient's skin and/or dispensing drug from the cartridge through the needle and/or retracting the needle post-injection. The user may control operation of the drug delivery device 1 through the touchscreen 3.

The touchscreen 3 enables a user interface with a customizable set of icons and controls, such as buttons 4 and interaction points, e.g. control elements 5 such as dials, radio buttons, slide controls, scroll bars, toggle buttons, drop down lists etc. This allows the control elements 5 and buttons 4 to be in alternative screen zones in different device modes; it also allows devices to have user interfaces tailored to specific user groups, e.g. geriatric and pediatric software versions. In addition, 'gestures' are possible with touchscreens 3, for controlling, scrolling, zooming, etc.; which are useful for devices with history and graph type functionality.

Figure 2:
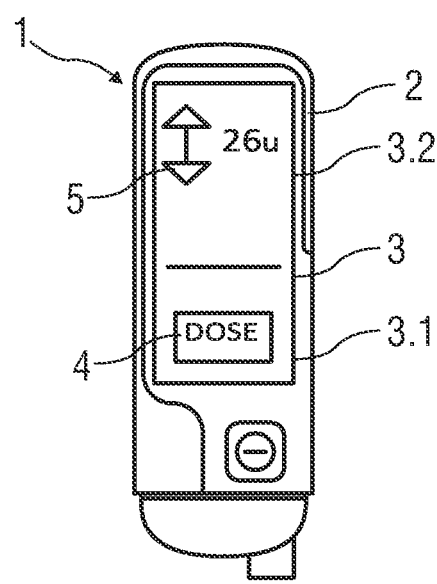
FIG. 2 is a schematic view of an exemplary embodiment of the electronically controlled drug delivery device with a touch screen split into two zones.

FIG. 2 is a schematic view of an exemplary embodiment of the electronically controlled drug delivery device 1. In this embodiment a control unit 6 of the touchscreen 3 splits the touchscreen 3 into two distinct zones 3.1, 3.2, which each serve a distinct purpose. A lower first zone 3.1 of the touchscreen 3 may act as a dose delivery button 4 and an upper second zone 3.2 of the touchscreen 3 may act as dose setting control element 5. This may prevent inadvertent activation of a drive mechanism of the drug delivery device 1.

Figure 3:
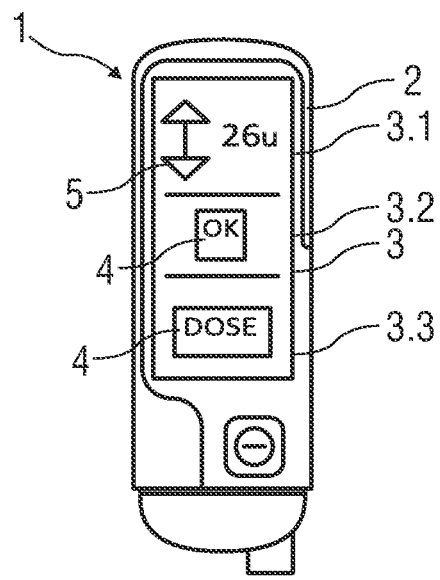
FIG. 3 is a schematic view of an exemplary embodiment of the electronically controlled drug delivery device with a touch screen split into three zones.

FIG. 3 is a schematic view of another exemplary embodiment of the electronically controlled drug delivery device 1. In this embodiment the touchscreen 3 is split into three distinct zones 3.1, 3.2, 3.3, which each serve a distinct purpose. An upper first zone 3.1 may be used for dose quantity setting by a control element 5, a middle second zone 3.2 may be used to confirm the set quantity by displaying an "OK" button 4 thus arming the drug delivery device 1, and a lower third zone 3.3 may provide a trigger button 4 for triggering delivery of the dose. The third zone 3.3 may be arranged to become active or live after the "OK" or "arm" button 4 in the second zone 3.2 has been pressed and remain inactive otherwise.

Figure 4:
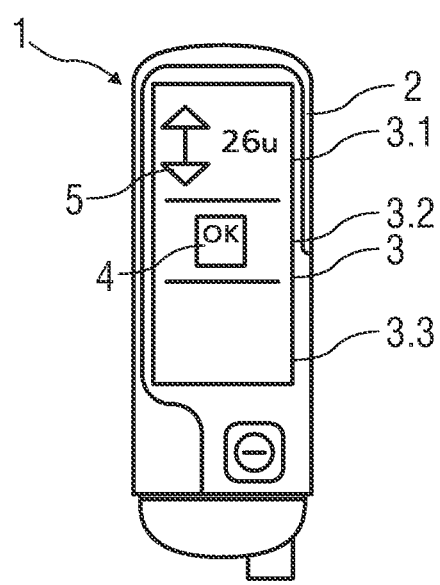
FIG. 4 is a schematic view of an exemplary embodiment of the electronically controlled drug delivery device with a touch screen split into three zones during dose setting.
Figure 5:
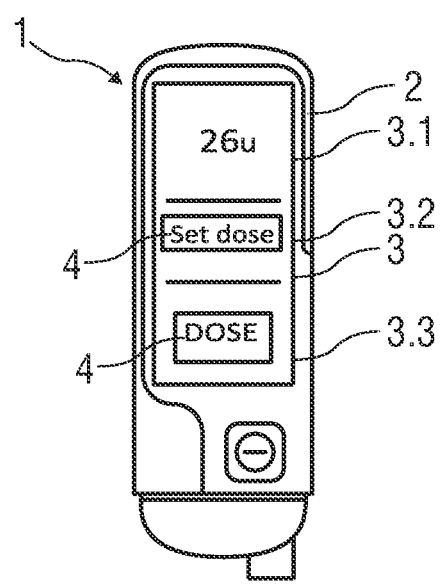
FIG. 5 is a schematic view of the embodiment of the electronically controlled drug delivery device of FIG. 4 after dose setting.

Alternative embodiments based upon the screen layout of the embodiments illustrated in FIG. 2 or 3 may also include a timer function, which requires a minimum time period between user steps, thereby eliminating the chance of the user accidentally swiping across more than one zone 3.1, 3.2, 3.3. The different zones 3.1, 3.2, 3.3 may also be context sensitive. For example, during dose setting only the first and second zones 3.1 and 3.2 may be visible or active as illustrated in FIG. 4, whilst after a dose is set only the second and third zones 3.2 and 3.3 are visible or active as illustrated in FIG. 5.

The touchscreen 3 may be implemented by any suitable technology, e.g. capacitive, resistive, optical or surface acoustic wave.

The invention may likewise be used with electronically controlled devices other than drug delivery devices 1.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des (B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group-Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by a, α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. An electronically controlled drug delivery device for administering a dose of a drug from a drug cartridge, comprising:
   a body with a touchscreen, wherein the body is configured to receive the drug cartridge; and
   a controller configured to control the touchscreen and operation of the drug delivery device related to delivery of the dose from the drug cartridge, wherein the controller is configured to split the touchscreen into at least three distinct zones, wherein the controller is configured to provide a control element for dose setting in one of the zones and to provide a button for confirming the set dose in another one of the zones and to provide a button for triggering delivery of the set dose of the drug in yet another one of the zones, wherein the controller is configured to render the button for triggering delivery of the set dose active only after operation of the button for confirming the set dose, wherein the controller comprises a timer for setting a time period, wherein the controller is configured to start the timer after operation of one of the zones and to switch the control element or button of at least one of the other zones from an inactive state to an active state after expiration of the set time period.

2. The electronically controlled drug delivery device according to claim 1, wherein the controller is configured to render the control element or button visible in the active state and invisible in the inactive state.

3. The electronically controlled drug delivery device according to claim 1, wherein the controller is configured to render the control element or button dimmed or shaded in the inactive state relative to its appearance in the active state.

4. The electronically controlled drug delivery device according to claim 1, wherein the touchscreen is arranged as a capacitive touchscreen.

5. The electronically controlled drug delivery device according to claim 1, wherein the touchscreen is arranged as a resistive touchscreen.

6. The electronically controlled drug delivery device according to claim 1, wherein the touchscreen is arranged as an optical touchscreen.

7. The electronically controlled drug delivery device according to claim 1, wherein the touchscreen is arranged as a surface acoustic wave touchscreen.

* * * * *